United States Patent [19]

Tokashiki et al.

[11] Patent Number: 5,447,853
[45] Date of Patent: Sep. 5, 1995

[54] METHOD OF PRODUCING USEFUL HIGH-MOLECULAR-WEIGHT SUBSTANCES BY CULTURING PROLIFEROUS ANIMAL CELLS, AND CULTURE SYSTEM THEREFOR

[75] Inventors: Michiyuki Tokashiki, Hino; Kimihiko Hamamoto, Hachioji, both of Japan

[73] Assignee: Teijin Limited, Osaka, Japan

[21] Appl. No.: 870,421

[22] Filed: Apr. 17, 1992

Related U.S. Application Data

[63] Continuation of Ser. No. 555,785, Jul. 23, 1990, abandoned, which is a continuation of Ser. No. 860,834, May 8, 1986, abandoned.

[30] Foreign Application Priority Data

May 9, 1985 [JP] Japan ................... 60-96770

[51] Int. Cl.⁶ ........................... C12P 21/08
[52] U.S. Cl. ................... 435/70.21; 435/70.1; 435/240.2; 435/172.2; 435/240.3; 435/240.31; 435/70.2; 530/387.1; 530/414
[58] Field of Search ............... 435/70.1, 70.2, 70.21, 435/240.2, 172.2, 240.26, 240.27, 240.3, 240.31; 530/387.1, 414

[56] References Cited

U.S. PATENT DOCUMENTS

4,420,398 12/1983 Castino ........................ 210/641
4,576,696 5/1986 Oertli ........................ 424/101

FOREIGN PATENT DOCUMENTS

0112152 6/1984 European Pat. Off. .
0112154 6/1984 European Pat. Off. .

OTHER PUBLICATIONS

Barnes et al. 1980 Cell 22, 649–655.
Kovar et al. 1984. Immunol. Lett. 7, 339–345.
Glacken et al. 1983 Trends Biotechnol. 1, 102–108.
Klein, J. 1982. in: *Immunol. The Science of Self-Nonself Discrimination*. John Wiley & Sons. New York, p. 190.
Kohler & Milstein, *Nature*.
Freshney, I. *Culture of Animal Cells.* 1983, Alan Liss Inc. New York, pp. 75 and 145.

*Primary Examiner*—Christopher S. F. Low
*Attorney, Agent, or Firm*—Wenderoth, Lind & Ponack

[57] ABSTRACT

A method of producing a useful high-molecular-weight substance by culturing animal cells capable of proliferation, which comprises (A) a culturing step of culturing said animal cells in suspension to form a suspension culture mixture containing the animal cells and a useful high-molecular-weight substance produced by the animal cells; (B) a separating step of separating the animal cells from the suspension culture mixture and withdrawing the culture medium; (C) a removing step of removing low-molecular-weight substances inhibiting the growth of the animal cells from the culture medium, said inhibitor substances being the metabolites of the animal cells and different from the useful high-molecular-weight substance; (D) a recycling step of recycling part or the whole of the culture medium left after removal of the growth-inhibiting low-molecular-weight substances to the culturing step (A); and (E) a recovering step of recovering the useful high-molecular-weight substance accumulated in the culture system. A culture system for culturing the animal cells is also described.

15 Claims, 1 Drawing Sheet

FIG. 1

METHOD OF PRODUCING USEFUL HIGH-MOLECULAR-WEIGHT SUBSTANCES BY CULTURING PROLIFEROUS ANIMAL CELLS, AND CULTURE SYSTEM THEREFOR

This application is a continuation of now abandoned application Ser. No. 07/555,785, filed Jul. 23, 1990, which is in turn a continuation of now abandoned Ser. No. 06/860,834, filed May 8, 1986, now abandoned.

This invention relates to a method of producing useful high-molecular-weight substances by culturing animal cells capable of proliferation (to be referred to hereinbelow as proliferous animal cells), and a culture system therefor.

Cell culture technology is important for the production of antiviral agents such as viral vaccines or interferons and biological chemical such as hormones. The recent production of monoclonal antibodies having the ability to bind to a specific protein as a target relies on the culture of a hybridoma obtained by fusing antibody-producing cells and myeloma, and the solution of problems associated with this technique is an industrially important subject.

Heretofore, cell culture has been carried out on a laboratory scale by using Petri dishes, test tubes, culture bottles, etc.

Some methods and apparatuses for cell culture have recently been suggested. They are roughly classified into anchorage-dependent culture systems and suspension culture systems selected according to the properties of a particular cell to be cultured.

A suspension cell culture method was proposed in which a spinner flask is given agitating function by a magnetic stirrer bar or by a mechanically driven impeller on a shaft (see U.S. Pat. Nos. 2,958,517 and 3,649,465).

Japanese Laid-Open Patent Publication No. 65180/1982 proposed a suspension culture apparatus in which at least one flexible sheet of a relatively large area supported on a rotatable shaft is used as an agitator and the desired gentle agitation is created for a certain kind of feeble cells such as human diploid cells by rotating the agitator sheet and thus causing it to undulate. In cell culture by this apparatus, the cells are cultured in a fixed amount of nutrients, and the growth of the cells stops while they are at relatively low cell densities.

To prevent the growth of cells from stopping at relatively low cell densities and to culture the cells in large quantities at high densities in suspension, there was proposed a so-called perfusion method comprising culturing cells while supplying a makeup culture medium to a culture vessel and in the meantime, discharging the spent medium containing a growth-inhibitor substance out of the vessel. In performing culture by this method, it is important to separate the spent medium efficiently from living cells in the suspension and discharge the spent medium out of the vessel, and thereby to maintain the growth environment for the cells in the vessel under optimum conditions.

Japanese Laid-Open Patent Publications Nos. 175877/1984 and 175878/1984 proposed a method which comprises feeding a culture medium containing cells to one surface of a semi-permeable membrane and allowing it to pass through the membrane, and removing waste products on the other side of the membrane or supplying nutrients to the culture medium containing cells from the other side of the membrane.

Preprints of the Third Symposium on Basic Technology for Next Generation Industry-Biotechnology (page 183, 1985) proposed a dialysis culture system having a double bottle structure. Specifically, this document describes a method which comprises culturing Namalva cells in an inner bottle having a bottom composed of a dialysis membrane, filling a dialysis medium in an outer bottle to such an extent that the bottom of the inner bottle is submerged in it, and removing cell growth inhibitor substances into the dialysis medium thereby to increase the density of the Namalva cells in the inner bottle.

According to the methods described in the above-cited Japanese Laid-Open Patent Publications Nos. 175877/1984 and 175878/1984 and Preprints, a large dialysis area must be secured in a place of actual culture.

Japanese Laid-Open Patent Publication No. 25483/1986 discloses a method and an apparatus for culturing anchorage-dependent cells. Specifically, it describes a method and an apparatus in which comprises a culture medium regulated in a culture environment regulating section is fed to a cell culture section filled with anchorage-dependent cells on carriers, the metabolites are separated and removed from the culture medium which has passed through the culture section, and the remainder is returned to the culture environment regulation section. The patent document describes that the above separation of the metabolites is carried out by ultrafiltration or dialysis.

Journal of Interferon Research, 2, No. 4, 533–541 (1982) discloses a method in which an induction suspension contained in a 2-liter round-bottom flask is recirculated through a 100,000 MWC (nominal molecular weight cutoff) filtration module, the retentate containing leukocytes and virus is recycled, the interferon-containing filtrate is fed to the reservoir and simultaneously recirculated in the 10,000 MWC filtration module, and the interferon-free solution is returned to the round-bottom flask.

In the production of useful substances by cell culture, it is industrially important to obtain the desired useful substances in high concentrations. Generally, the concentration of a useful substance produced by cells in a culture medium in cell culture is very low, and complex procedures are required to separate the useful substance from the culture medium and purify it. This is one cause of the reduction of the recovery ratio and the increase of the cost. The method described in Journal of Interferon Research, 2, No. 4, 533–541 (1982) cited above gives a solution having a high interferon concentration and therefore may be said to be an industrially advantageous method.

The concentration of the useful substance can be increased to some extent by performing culture at a high cell density. To culture cells at a high density, it is necessary, as stated hereinabove, to supply a makeup medium while discharging the spent culture medium out of the culture system. Thus, there is naturally a limit to the increase of the concentration of useful substances in the technique of culturing cells at a high density.

It is an object of this invention to provide a novel method for producing a useful high-molecular-weight substance which comprises culturing animal cells in suspension.

It is another object of this invention to provide a method for culturing proliferous animal cells in suspension, in which a useful high-molecular-weight substance produced by the cells can be obtained in an increased concentration.

Still another object of this invention is to provide an industrially advantageous culture system for obtaining a culture fluid containing a useful high-molecular-weight substance in a high concentration.

Yet another object of this invention is to provide a simple, industrially valuable method of cell culture for obtaining an antibody as a useful high-molecular-weight substance in a high concentration.

A further object of this invention is to provide a method of producing a useful high-molecular-weight substance economically with industrial advantage by removing substances inhibiting the growth of proliferous animal cells, obtaining a culture fluid containing a growth promoting substance, and recycling the culture fluid to the culture system.

Other objects of this invention along with its advantages will become apparent from the following description.

The objects and advantages of this invention are achieved by a method of producing a useful high-molecular-weight substance by culturing proliferous animal cells, which comprises (A) a culturing step of culturing proliferous animal cells in suspension to form a suspension culture mixture containing the proliferous animal cells and a useful high-molecular-weight substance produced by the animal cells;

(B) a separating step of separating the animal cells from the suspension culture mixture and withdrawing the culture medium;

(C) a removing step of removing low-molecular-weight substances inhibiting the growth of the animal cells from the culture medium; said inhibitor substances being the metabolites of the animal cells and different from the useful high-molecular-weight substance;

(D) a recycling step of recycling part or the whole of the culture medium left after removal of the growth-inhibiting low-molecular-weight substances to the culturing step (A); and (E) a recovering step of recovering the useful high-molecular-weight substance accumulated in the culture system.

Since the method of this invention includes a step of recycling the culture medium left after removal of the growth-inhibiting low-molecular-weight substances, the culture can be carried out at a high cell density (including the case where the cells grow by culture and achieve a high cell density and the case where the cell density is high from the outset of the culture), and consequently, a culture medium containing the useful high-molecular-weight substance in a high concentration can be obtained. It has also been found for the first time by the present inventors that a high cell density can be achieved in a culture medium containing the useful high-molecular-weight substance in a high concentration. This finding has led to the successful production of a culture fluid containing the useful high-molecular-weight substance in an increasingly higher concentration.

The method of this invention comprises the five steps (A) to (E). As is clear from step (A), the method of this invention is applicable to culture in suspension. The culture in suspension denotes various types of floating culture in which cells are grown in an aqueous medium while they are floating by themselves, or on microcarriers, or in microcapsules. The present invention can be advantageously applied to the culturing of cells while the cells by themselves are floating.

The animal cells to be cultured in the culturing step of this invention may be those which can proliferate in suspension and produce useful high-molecular-weight substances. They include not only natural proliferous animal cells, but also those animal cells which are modified artificially or by gene manipulation, such as hybridoma cells. The cells may be proliferous cells derived from lymphocytes which produce lymphokine such as interleukin, diploid cells producing useful biologically active substances such as interferons (IFN), or proliferous cells producing various monoclonal antibodies. The invention is specially suitable for obtaining monoclonal antibodies in high concentrations by the culturing of cells capable of producing such monoclonal antibodies.

In the cell culturing step (A) of the method of this invention, cells are cultured while floating in the culture medium in a culture vessel. As stated above, the culture includes the case where the cells proliferate during the culture, and the case where the cells do not substantially proliferate during the culture. The culture medium is prepared by adding components normally used in cell culture, such as inorganic salts, vitamins, coenzymes, glucose, amino acids and antibiotics. Serum may be added to the culture medium, or a "cell-free" medium may also be used.

Figure 1:
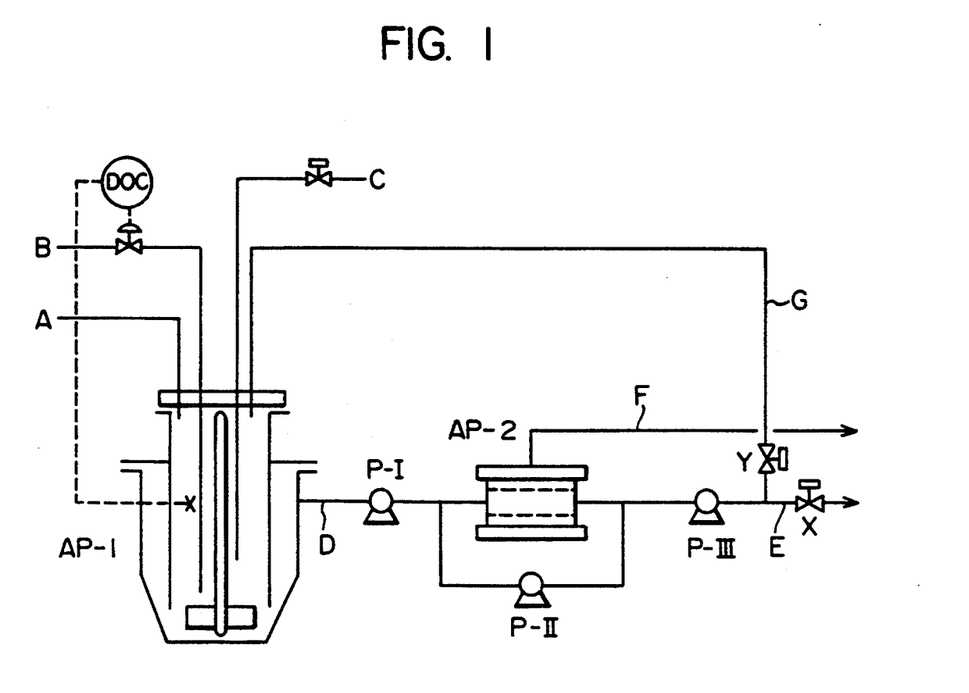

The method of this invention includes the separating step (B) in which the animal cells are separated from the suspension culture mixture and the culture medium is withdrawn. The separation of the animal cells can be effected in the culture vessel (for example, in the suspension culture mixture) as shown in FIG. 1. Alternatively, it is possible to withdraw the suspension culture mixture from the culture vessel, separate the animal cells from the suspension culture mixture outside the culture tank, and recycle the animal cells to the culture vessel. In any case, the separation may be carried out by any of various methods by which the grown cells do not substantially come into the separated culture medium. For example, the separating step (B) is carried out by gravity sedimentation, centrifugal sedimentation, or filtration. The gravity sedimentation can be carried out, for example, by providing a settling zone in the culture vessel as shown in FIG. 1, separating the animal cells from the culture medium by gravity in the settling zone to settle the animal cells, and withdrawing the supernatant culture medium out of the culture vessel. The centrifugal sedimentation can be carried out by centrifugation. The filtration may be carried out by using various filters such as a rotating filter, a fixed filter, or a hollow fiber module. For example, for the separation of hybridoma cells from the culture medium, a filter having an opening diameter of not more than 5 micrometers is conveniently used since the hybridoma cells have a size of at least about 10 micrometers.

The separation of the animal cells from the culture medium in step (B) is carried out in an aseptic condition.

The culture medium separated in the separating step (B) contains low-molecular-weight substances inhibiting the growth of the animal cells, which are metabolites of the animal cells. The low-molecular-weight substances are removed in step (C) because when they are accumulated in some amounts in the culture system, the animal cells no longer proliferate, or their proliferation is reduced. The removal of the low-molecularweight substances may be carried out by, for example, ultrafiltration, dialysis or adsorption. The growth inhibiting low-molecular-weight substances usually have a molecular weight of 10,000 at the highest. Usually, a useful high-molecular-weight substance having a molecular weight of more than 10,000 is produced in the suspension culture mixture formed in the culturing step (A). Hence, in the removing step (C), the growth inhibiting low-molecular-weight substances alone can be removed while leaving the useful high-molecular-weight compound.

Examples of the useful high-molecular-weight substances are proteins including glycoproteins, such as immunoglobulins. The immunoglobulins are, for example IgG and IgM. The immunoglobulins may be human immunoglobulins or immunoglobulins of other animals.

When the useful high-molecular-weight substance is IgG and the removing step (C) is carried out by ultrafiltration, it is convenient to use an ultrafiltration membrane substantially impermeable to substances having a molecular weight of about 150,000, for example an ultrafiltration membrane having a fractionating molecular weight of about 10,000 to 50,000. When the useful high-molecular-weight substance is IgM, it is convenient to use an ultrafiltration membrane substantially impermeable to substances having a molecular weight of about 1,000,000, for example an ultrafiltration membrane having a fractionating molecular weight of about 10,000 to 500,000. The use of the aforesaid ultrafiltration membranes enables a culture medium free from the cell growth inhibiting substances to be obtained without permitting the permeation of useful high-molecular-weight substances such as IgG and IgM.

Ultrafiltration in step (C) is preferably a method which readily permits washing and regeneration of a filtration surface, namely which has a small holdup. It may be of a hollow fiber, spiral, tubular, or plate-and-frame type, for example. The hollow fiber type and the plate-and-frame type are desirable. The removing step (C) may also be carried out by dialysis or adsorption in a manner known per se.

In the method of this invention, part or the whole of the culture medium obtained from step (C) is recycled to the culturing step (A). When, for example, a monoclonal antibody is produced in step (A) in accordance with the method of this invention and a fraction containing it is separated in step (C) and recycled to step (A), the concentration of the monoclonal antibody in the suspension culture mixture becomes high (for example, at least 1 mg/ml). This increase in concentration, however, does not particularly exert a deleterious effect on the growth and proliferation of the cells themselves.

In the recycling step (D), the ratio of recycling the fraction containing the useful high-molecular-weight substance separated in step (C) to the culturing step (A) is determined while monitoring the concentration of the useful substance in the suspension culture mixture and the state of the growth of the cells. Specifically, when the cell density and the concentration of the useful substance in the suspension culture mixture in step (A) are both low, it is desirable to recycle the whole or nearly whole of the culture medium from step (C). On the other hand, as the concentration of the useful substance in the suspension culture mixture increases, it is desirable to decrease the ratio of recycling and withdraw the remainder out of the culture system.

The useful high-molecular-weight substance accumulated in the culture system as a result of practising the steps (A) to (D) of the method of this invention is withdrawn from the culture system and recovered after one or a plurality of cycles of steps (A) to (B). It can be taken out from part of the culture medium from step (C), or from the culture medium of step (A) containing the animal cells. It can be taken out either continuously or intermittently. The continuous withdrawal is particularly desirable.

The method of this invention can be carried out by using a serum-containing medium as the suspension culture mixture in step (A), or a substantially cell-free medium. The serum contains a substance which promotes the growth of animal cells. Thus, one advantage of the method of this invention is that even after the growth inhibiting low-molecular-weight substances have been removed in step (C), the growth promoting substance remains, and by recycling the culture medium to step (A) in the recycling step (D), the growth promoting substance of the serum which is expensive can be utilized.

When the culture is carried out by using a serum-containing medium, the proportion of serum used can be drastically decreased if the growth inhibiting substances are removed in step (C) by using an ultrafiltration membrane having a fractionating molecular weight of 10,000 and the remainder is recycled to the culturing step (A).

When the culturing step (A) is carried out using a substantially serum-free medium, a growth promoting substance such as transferin, insulin, albumin, ethanoalamine or selenium compounds is usually added to the culture medium. Of these growth promoting substances, relatively high-molecular-weight compounds such as transferin, insulin or albumin can advantageously be caused to remain in the culture medium even after the growth inhibiting low-molecular-weight substances are removed in step (C).

For example, when the culture is carried out using a serum-free medium (e.g., ITES), the use of a separation membrane having a fractionating molecular weight of 10,000 enables transferin as a growth promoting substance to be recovered at a high ratio and reused, or insulin to be recovered partially. The use of a separation membrane having a fractionating molecular weight of 1,000 enables not only transferin but also insulin to be recovered at higher ratios and recycled to step (A).

In the practice of the method of this invention, it is desirable, but not always necessary, to supply the makeup culture medium and discharge the spent culture medium in such a manner that the liquid level of the culture vessel is maintained nearly constant. Supply of the makeup culture medium and discharge of the spent culture medium may be carried out independently from each other in a continuous or intermittent manner.

Oxygen is supplied in the method of this invention in order to maintain the oxygen concentration in the suspension culture mixture constant. This may be effected by directly supplying oxygen or an oxygen-containing gas into the suspension culture mixture, or by other supplying means. For example, it may be effected by using an oxygen carrier which may be a liquid compound that is substantially immiscible with water and can dissolve oxygen. Examples of such a compound are various fluorocarbons used as a material for artificial blood. When such fluorocarbons are used as means for supplying oxygen, a fluorocarbon containing oxygen dissolved therein may be added in liquid droplets or as a thin film to the suspension culture mixture from above.

For efficient culture, it is necessary to supply the makeup culture medium and oxygen uniformly to the suspension, and meanwhile discharge the culture medium out of the vessel. For this purpose, the suspension is desirably agitated with good efficiency. The agitation may be carried out by a mechanical agitating method using the rotation of an agitating vane, a method based on a draft effect using a guide cylinder, or a method by which oxygen supply by means of an oxygen carrier and agitation are simultaneously effected, or a combination of two or more such agitating methods.

The ratio of the makeup culture medium to the effective culture volume (V) of the culture vessel (the amount of the makeup culture medium/V) is suitably 0.2 to 10, preferably 0.5 to 5, per day.

The method of this invention can be advantageously carried out by a culture system in accordance with this invention for culturing animal cells capable of proliferation in suspension, said system comprising (1) a culture vessel for culturing in suspension said animal cells having the ability to produce a useful high-molecular-weight substance, (2) a separating means for separating the animal cells from the resulting suspension culture mixture containing the animal cells and withdrawing the culture medium free of the animal cells, (3) a removing means for removing low-molecular-weight substances from the culture medium free from the animal cells, said low-molecular-weight substances being metabolites of the animal cells and inhibiting the growth of the animal cells, (4) a conveying means for conveying the culture medium free from the animal cells to the removing means, (5) means for recycling the culture medium left after removal of the growth-inhibiting low-molecular-weight substances to the culture vessel, and (6) means for withdrawing the culture medium for recovery of the useful high-molecular-weight substance.

Thus, the present invention makes it possible to obtain a culture medium containing a useful high-molecular-weight substance, particularly a monoclonal antibody, in a high concentration by a relatively simple means. In a preferred embodiment, expensive substances such as serum and growth-promoting substances can be greatly saved.

The following Examples illustrate the present invention in greater detail.

EXAMPLE 1

(1) Culture apparatus

A culture system of the type shown in FIG. 1 was used. The culture vessel (AP-1) contained a settling zone provided inwardly of its outer wall by partitioning wall, and a discharge opening at its top for discharging the culture fluid. The net volume of the culture tank was about 200 ml. The system included a plate-and-frame type ultrafiltration device AP-2 containing an ultrafiltration membrane (made by Millipore Corporation; PSAC OLC 05 with a fractionating molecular weight of 1,000).

(2) Culture medium

A mixture of RPMI 1640 medium, HAM F-12 medium and Dulbecco's modified Eagle medium in a ratio of 2:1:1 (to be referred to as RDF) was used as a basal medium, and insulin, transferin, ethanolamine and sodium selenite were added as growth-promoting factors. The amount of ethanolamine added was 10 micrograms/ml, and the amount of sodium selenite added was $2\times10^{-8}$ mole/liter. The amount of insulin was 2 micrograms/ml for medium $\alpha$-1 and 0.2 microgram/ml for medium $\beta$-1, and the amount of transferin was 10 micrograms/ml for medium $\alpha$-1, and 1 microgram/ml for medium $\beta$-1.

(3) Culture method and results

The culture vessel was sterilized by autoclaving, and the culture medium $\alpha$-1 was fed into it so that the net culture volume became about 200 ml. Mouse-mouse hybridoma cells 4C10B6 derived from mouse myeloma cell P3U1 as parent cells were seeded in the culture medium at a density of $4\times10^5$/ml. These hybridoma cells were capable of producing IgG. Oxygen gas containing 5% of carbon dioxide gas dissolved in it was fed into the culture vessel through a blowing nozzle B while being automatically controlled so that the dissolved oxygen concentration became 3 ppm. The culture medium in the culture vessel was maintained at 37° C. The culture vessel was fitted with a marine-type agitating vane, and the agitating speed was 60 rpm.

For four days after seeding, the cells were cultured batchwise. As shown in Table 1, on the fourth day after the start of culture, the cell density reached $1.1\times10^6$ cells/ml. This cell density was judged to be highest attainable by batchwise culture, and therefore, perfusion was started. As a measure of perfusion, the rate of replacement of the net culture volume by the makeup culture medium per day was determined, and shown in Table 1 together with the experimental results.

Specifically, the valve X was opened and the valve Y was closed by operating the pumps P-I, P-II and P-III, and the culture fluid separated from the cells in the culture vessel was withdrawn from line D. The same amount of the makeup medium $\alpha$-1 was continuously introduced from line A. The liquid which passed through the ultrafiltration membrane was withdrawn from line F, and the liquid which did not pass through the membrane was withdrawn from the system from line E. With the lapse of time, the cell density rose and reached $12\times10^6$ cells/ml on the 10th day. At this point, the valve X was closed and the valve Y was opened. The liquid which did not pass through the ultrafiltration membrane was recycled to the culture vessel through line G. At the same time, the medium $\alpha$-1 fed from line A was changed to the medium $\beta$-1. From the 10th day onward, the culture mixture containing the cells were withdrawn every day out of the system in an amount of 20 ml which corresponded to about 10% of the net culture volume.

The foregoing culturing operation was continued for 26 days, and the results are shown in Table 1.

TABLE 1

| Culture time (days) | Open valves | Rate of replacement (times/day) | Withdrawal of the culture mixture (amount withdrawn/day) Culture volume | Culture medium | Cell density ($10^6$ cells/ml) | Concentration of antibody in the culture fluid (mg/ml) |
|---|---|---|---|---|---|---|
| 0 |   | 0 | 0 | α-1 | 0.4 | 0 |
| 2 |   | 0 | 0 | α-1 | 0.7 | 0.01 |
| 4 | X | 1.0 | 0 | α-1 | 1.1 | 0.03 |
| 6 | X | 2.0 | 0 | α-1 | 3.1 | 0.04 |
| 8 | X | 2.0 | 0 | α-1 | 8.2 | 0.05 |
| 10 | Y | 2.5 | 0.1 | β-1 | 12 | 0.08 |
| 12 | Y | 2.5 | 0.1 | β-1 | 10 | 0.30 |
| 14 | Y | 2.5 | 0.1 | β-1 | 11 | 0.50 |
| 16 | Y | 3.0 | 0.1 | β-1 | 9 | 0.72 |
| 18 | Y | 3.0 | 0.1 | β-1 | 13 | 0.89 |
| 20 | Y | 3.0 | 0.1 | β-1 | 15 | 1.09 |
| 22 | Y | 3.0 | 0.1 | β-1 | 14 | 1.31 |
| 24 | Y | 3.0 | 0.1 | β-1 | 15 | 1.55 |
| 26 | Y | 3.0 | 0.1 | β-1 | 14 | 1.78 |

EXAMPLE 2

Example 1 was repeated except that human IgA-producing mouse-human hybridoma 4H11 cells obtained by fusing mouse myeloma P3U1 and human B cells were used as the cells; the culture media were changed to media containing fetal calf serum (FCS) (10% for α-2, and 1% for β-2); and that an ultrafiltration membrane having a fractionating molecular weight of 10,000 (PTGC OLC 05, Millipore Corporation) was used instead of the ultrafiltration membrane used in Example 1. The results are shown in Table 2.

by fusing mouse myeloma P3U1 with human B cells were used as the cells; a serum-free medium obtained by adding insulin, transferin, ethanolamine, selenous acid and BSA (bovine serum albumin) to the basal medium RDF [α-3: ITES+BSA (5 mg/ml)+RDF, 10 micrograms/ml of insulin and 20 micrograms/ml of transferin; β-3: ITES+BSA (0.5 mg/ml)+RDF, 2 micrograms/ml of insulin and 2 micrograms/ml of transferin] was used as the culture medium; and an ultrafiltration membrane having a fractionating molecular weight of 10,000 (CTGC OLC 05, Millipore Corporation) was used instead of the ultrafiltration membrane in Example 1. The results are shown in Table 3.

TABLE 2

| Culture time (days) | Open valves | Rate of replacement (times/day) | Withdrawal of the culture mixture (amount withdrawn/day) Culture volume | Culture medium | Cell density ($10^6$ cells/ml) | Concentration of antibody in the culture fluid (mg/ml) |
|---|---|---|---|---|---|---|
| 0 |   | 0 | 0 | α-2 | 0.4 | 0 |
| 2 |   | 0 | 0 | α-2 | 0.81 | 0.01 |
| 4 | X | 0.5 | 0 | α-2 | 1.2 | 0.02 |
| 6 | X | 1.0 | 0 | α-2 | 3.0 | 0.03 |
| 8 | X | 1.5 | 0 | α-2 | 6.5 | 0.04 |
| 10 | X | 2.0 | 0 | α-2 | 8.8 | 0.05 |
| 12 | Y | 2.5 | 0.1 | β-2 | 11 | 0.07 |
| 14 | Y | 3.0 | 0.1 | β-2 | 13 | 0.23 |
| 16 | Y | 3.0 | 0.1 | β-2 | 12 | 0.40 |
| 18 | Y | 3.0 | 0.1 | β-2 | 14 | 0.59 |
| 20 | Y | 3.0 | 0.1 | β-2 | 12 | 0.70 |
| 22 | Y | 3.0 | 0.1 | β-2 | 11 | 0.88 |
| 24 | Y | 3.0 | 0.1 | β-2 | 14 | 1.0 |

EXAMPLE 3

Example 1 was repeated except that human IgG-producing mouse-human hybridoma D34.3.1 cells obtained

TABLE 3

| Culture time (days) | Open valves | Rate of replacement (times/day) | Withdrawal of the culture mixture (amount withdrawn/day) Culture volume | Culture medium | Cell density ($10^6$ cells/ml) | Concentration of antibody in the culture fluid (mg/ml) |
|---|---|---|---|---|---|---|
| 0 |   | 0 | 0 | α-3 | 0.4 | 0 |
| 2 |   | 0 | 0 | α-3 | 0.75 | 0 |
| 4 | X | 0.5 | 0 | α-3 | 1.0 | 0.01 |
| 6 | X | 1.0 | 0 | α-3 | 2.6 | 0.012 |
| 8 | X | 1.5 | 0 | α-3 | 5.5 | 0.025 |
| 10 | X | 2.0 | 0 | α-3 | 7.9 | 0.030 |
| 12 | Y | 2.5 | 0 | β-3 | 10 | 0.030 |
| 14 | Y | 3.0 | 0.1 | β-3 | 13 | 0.095 |
| 16 | Y | 3.0 | 0.1 | β-3 | 14 | 0.17 |
| 18 | Y | 4.0 | 0.1 | β-3 | 16 | 0.27 |
| 20 | Y | 4.0 | 0.1 | β-3 | 17 | 0.33 |
| 22 | Y | 4.0 | 0.1 | β-3 | 15 | 0.43 |
| 24 | Y | 4.0 | 0.1 | β-3 | 14 | 0.51 |
| 26 | Y | 4.0 | 0.1 | β-3 | 16 | 0.59 |

TABLE 3-continued

| Culture time (days) | Open valves | Rate of replacement (times/ day) | Withdrawal of the culture mixture (amount withdrawn/day) Culture volume | Culture medium | Cell density ($10^6$ cells/ml) | Concentration of antibody in the culture fluid (mg/ml) |
| --- | --- | --- | --- | --- | --- | --- |
| 28 | Y | 4.0 | 0.1 | β-3 | 16 | 0.68 |

EXAMPLE 4

(1) Culture apparatus

The culture system shown in FIG. 1 was used. The culture vessel (AP-1) had an inner capacity of about 200 ml, and the ratio of the height (H) of the culture vessel to its diameter (D), H/D, was 2:1. The culture vessel had a settling zone on which no substantial agitating effect was exerted. The V/S in this zone was 5.3 cm, and h was 8 cm. The culture apparatus also included a plate-and-frame type ultrafiltration device AP-2 having an ultrafiltration membrane (PSAC OLC 05 made by Millipore Corporation) having a fractionation molecular weight of 10,000.

(2) Culture medium

A mixture composed of RPMI 1640 medium, HAM F-12 medium and Dulbecco's modified Eagle medium in a ratio of 2:1:1 and also containing glucose and amino acids (to be referred to as eRDF) was used as a basal medium, and insulin, transferin, ethanolamine and sodium selenite were added as growth-promoting factors. The amount of ethanolamine added was 10 μM, and the amount of sodium selenite added was $2 \times 10^{-8}$ mole/liter. The amount of insulin was 9 micrograms/ml for medium α-4 and 0.45 microgram/ml for medium β-4, and the amount of transferin was 10 micrograms/ml for medium α-4, and 0.5 microgram/ml for medium β-4.

(3) Culture method

The culture vessel was sterilized by autoclaving, and the culture medium α-4 was fed into it so that the net culture volume became about 120 ml. Mouse-human hybridoma cells H2 derived from mouse myeloma cell P3U1 as parent cells were seeded in the culture medium at a density of $6 \times 10^5$/ml. These hybridoma cells were capable of producing IgG. Oxygen gas containing 5% of carbon dioxide gas dissolved in it was fed into the culture vessel through a blowing nozzle B while being automatically controlled so that the dissolved oxygen concentration became 3 ppm. The culture medium in the culture vessel was maintained at 37° C. The culture vessel was fitted with a marine-type agitating vane, and the agitating speed was 60 rpm.

For one day after seeding, the cells were cultured batchwise, and perfusion was started on the first day. As a measure of perfusion, the rate of replacement of the net culture volume by the makeup culture medium per day was determined, and shown in Table 1 together with the experimental results.

Specifically, the valve X was opened and the valve Y was closed by operating the pumps P-I, P-II and P-III, and the culture fluid separated from the cells in the culture vessel was withdrawn from line D. The same amount of the makeup medium α-4 was continuously introduced from line A. The liquid which passed through the ultrafiltration membrane was taken out from line F, and the liquid which did not pass through the membrane was taken out of the system from line E. With the lapse of time, the cell density rose and reached $6.6 \times 10^6$ cells/ml on the 6th day. Since the cell density did not increase till the 9th day, the valve X was closed and the valve Y was opened. The liquid which did not pass through the ultrafiltration membrane was recycled to the culture vessel through line G. At the same time, the medium β-4 was fed from line A instead of the medium α-4.

(4) Culture results

The above culturing operation was continued for 48 days, and the results are shown in Table 4.

TABLE 4

| Culture time (days) | Open valves | Rate of replacement (times/ day) | Culture medium | Cell density ($10^6$ cells/ml) | Concentration of antibody in the culture fluid (mg/ml) |
| --- | --- | --- | --- | --- | --- |
| 0 |  | 0 | α-4 | 0.6 | — |
| 2 | X | 2 | α-4 | 1.0 | — |
| 4 | X | 4 | α-4 | 2.5 | — |
| 6 | X | 4 | α-4 | 6.6 | — |
| 8 | X | 7 | α-4 | 6.5 | — |
| 10 | Y | 4 | β-4 | 6.5 | 0.03 |
| 12 | Y | 4 | β-4 | 9.5 | 0.05 |
| 14 | Y | 4 | β-4 | 11 | 0.06 |
| 16 | Y | 4 | β-4 | 12 | 0.12 |
| 18 | Y | 4 | β-4 | 13 | 0.23 |
| 20 | Y | 4 | β-4 | 18 | 0.34 |
| 22 | Y | 4 | β-1 | 15 | 0.40 |
| 24 | Y | 4 | β-4 | 26 | 1.0 |
| 26 | Y | 4 | β-4 | — | 1.2 |
| 28 | Y | 4 | β-4 | 5.4 | 1.2 |
| 30 | Y | 4 | β-4 | 6.2 | 1.3 |
| 32 | Y | 4 | β-4 | 10 | 1.5 |
| 34 | Y | 4 | β-4 | 11 | 1.8 |
| 36 | Y | 4 | β-4 | 2.1 | 1.7 |
| 38 | Y | 4 | β-4 | 1.9 | 1.6 |
| 40 | Y | 4 | β-4 | 4.3 | 1.6 |
| 42 | Y | 4 | β-4 | 8.2 | 1.6 |
| 44 | Y | 4 | β-4 | 12 | 1.6 |

TABLE 4-continued

| Culture time (days) | Open valves | Rate of replacement (times/ day) | Culture medium | Cell density ($10^6$ cells/ml) | Concentration of antibody in the culture fluid (mg/ml) |
| --- | --- | --- | --- | --- | --- |
| 46 | Y | 4 | β-4 | 19 | 1.7 |
| 48 | Y | 4 | β-4 | 19 | 2.0 |

EXAMPLE 5

Example 4 was repeated except that human IgG-producing mouse-human hybridoma cells C41-2-1 were used as the cells, and a culture medium composed of ITES, eRDF and polyvinylpyrrolidone molecular weight about 40,000; a product of Wako Pure Chemicals, Ltd.] (α-5: ITES+eRDF, 0.1% PVP K-30, 9 micrograms/ml of insulin, 10 micrograms/ml of transferin; β-5: ITES+eRDF, 0.45 microgram/ml of insulin, 0.5 microgram/ml of transferin) was used as the culture medium. The results are shown in Table 5.

TABLE 5

| Culture time (days) | Open valves | Rate of replacement (times/ day) | Culture medium | Cell density ($10^6$ cells/ml) | Concentration of antibody in the culture fluid (mg/ml) |
| --- | --- | --- | --- | --- | --- |
| 0 |  | 0 | α-5 | 0.8 | — |
| 2 | X | 2 | α-5 | 1.3 | — |
| 4 | X | 4 | α-5 | 3.4 | — |
| 6 | X | 6 | α-5 | 4.6 | — |
| 8 | X | 6 | α-5 | 5.8 | — |
| 10 | Y | 6 | β-5 | 9.4 | — |
| 12 | Y | 6 | β-5 | 5.8 | 0.05 |
| 14 | Y | 6 | β-5 | 6.4 | 0.07 |
| 16 | Y | 6 | β-5 | 6.8 | 0.09 |
| 18 | Y | 6 | β-5 | 11 | 0.11 |
| 20 | Y | 6 | β-5 | 9.2 | 0.14 |
| 22 | Y | 6 | β-5 | 9.2 | 0.16 |
| 24 | Y | 6 | β-5 | 10 | 0.20 |

EXAMPLE 6

Example 4 was repeated except that the following culture media were used.

Medium α-6
Composed of ITES, BSA (5 mg/ml) and eRDF with 9 micrograms/ml of insulin and 10 micrograms/ml of transferin.

Medium β-6
Composed of ITES, BSA (0.25 mg/ml) and eRDF with 2 micrograms of insulin and 0.5 microgram/ml of transferin.

The results are shown in Table 6.

TABLE 6

| Culture time (days) | Open valves | Rate of replacement (times/ day) | Culture medium | Cell density ($10^6$ cells/ml) | Concentration of antibody in the culture fluid (mg/ml) |
| --- | --- | --- | --- | --- | --- |
| 0 | X | 0.5 | α-6 | 0.23 | — |
| 2 | X | 1.5 | α-6 | 0.52 | — |
| 4 | X | 2.5 | α-6 | 1.3 | 12 |
| 6 | X | 3.2 | α-6 | 2.9 | 21 |
| 8 | Y | 4.0 | β-6 | 4.8 | 30 |
| 10 | Y | 4.0 | β-6 | 6.4 | 100 |
| 12 | Y | 4.0 | β-6 | 6.8 | 210 |
| 14 | Y | 4.0 | β-6 | 7.2 | 260 |
| 16 | Y | 4.0 | β-6 | 10.1 | 350 |
| 18 | Y | 4.0 | β-6 | 13 | 610 |
| 20 | Y | 4.0 | β-6 | 11 | 620 |
| 22 | Y | 4.0 | β-6 | 13 | 770 |

COMPARATIVE EXAMPLE 1

Example 6 was repeated except that the culture medium was not recycled, and the medium α-6 was always used. The results are shown in Table 7.

TABLE 7

| Culture time (days) | Open valves | Rate of replacement (times/ day) | Culture medium | Cell density ($10^6$ cells/ml) | Concentration of antibody in the culture fluid (mg/ml) |
| --- | --- | --- | --- | --- | --- |
| 0 | X | 0.5 | α-6 | 0.8 | — |
| 2 | X | 1.9 | " | 1.6 | 22 |

TABLE 7-continued

| Culture time (days) | Open valves | Rate of replacement (times/ day) | Culture medium | Cell density ($10^6$ cells/ml) | Concentration of antibody in the culture fluid (mg/ml) |
| --- | --- | --- | --- | --- | --- |
| 4  | X | 4.0 | " | 2.5 | 19 |
| 6  | X | 6.0 | " | 4.7 | 20 |
| 8  | X | 7.0 | " | 6.0 | 30 |
| 10 | X | "   | " | 9.4 | 44 |
| 12 | X | "   | " | 12  | 51 |
| 14 | X | "   | " | 11  | 49 |
| 16 | X | "   | " | 13  | 54 |
| 18 | X | "   | " | 9   | 51 |
| 20 | X | "   | " | 12  | 49 |
| 22 | X | "   | " | 12  | 51 |
| 24 | X | "   | " | 11  | 52 |

COMPARATIVE EXAMPLE 2

Comparative Example 1 was repeated except that after 14th day from the start of culturing, the culture medium was replaced by the medium β-6. The results are shown in Table 8.

After the medium was changed over to the medium β-6, the living cells decreased with time, and on the 22nd day, the cell density was less than $10^6$ cells/ml. The culturing was therefore stopped.

TABLE 8

| Culture time (days) | Open valves | Rate of replacement (times/ day) | Culture medium | Cell density ($10^6$ cells/ml) | Concentration of antibody in the culture fluid (mg/ml) |
| --- | --- | --- | --- | --- | --- |
| 0  | X  | 0.5 | α-6 | 1.0 | — |
| 2  | X  | 1.9 | "   | 1.7 | 23 |
| 4  | X  | 4.0 | "   | 2.7 | 20 |
| 6  | X  | 6.0 | "   | 5.1 | 23 |
| 8  | X  | 7.0 | "   | 6.5 | 32 |
| 10 | X  | "   | "   | 9.1 | 41 |
| 12 | X  | "   | "   | 11  | 48 |
| 14 | X  | "   | β-6 | 12  | 51 |
| 16 | X  | "   | "   | 7.2 | 19 |
| 18 | X  | "   | "   | 4.1 | — |
| 20 | X  | "   | "   | 1.4 | — |
| 22 | X  | "   | "   | 0.6 | — |

EXAMPLE 7

Example 6 was repeated except that IgG-producing hybridoma cells V-6 obtained by fusing mouse myeloma cells P3U1 with human B cells were used as the cells. The results are shown in Table 9.

TABLE 9

| Culture time (days) | Open valves | Rate of replacement (times/ day) | Culture medium | Cell density ($10^6$ cells/ml) | Concentration of antibody in the culture fluid (mg/ml) |
| --- | --- | --- | --- | --- | --- |
| 0  | X | 0   | α-6 | 1.0 | — |
| 2  | X | 2.0 | "   | 1.6 | — |
| 4  | X | 4.0 | "   | 2.0 | — |
| 6  | X | 4.0 | "   | 3.4 | — |
| 8  | X | 5.5 | "   | 3.7 | — |
| 10 | X | 5.5 | "   | 4.0 | — |
| 12 | X | 5.5 | "   | 6.8 | — |
| 14 | X | 7.8 | "   | 12  | 8 |
| 16 | Y | 3.2 | β-6 | 6.8 | 6 |
| 18 | Y | 3.2 | "   | 7.2 | 14 |
| 20 | Y | 3.2 | "   | 6.2 | 35 |
| 22 | Y | 3.2 | "   | 9.0 | — |
| 24 | Y | 3.5 | "   | 7.0 | 98 |
| 26 | Y | 3.5 | "   | 15  | — |
| 28 | Y | 3.5 | "   | 16  | 170 |
| 30 | Y | 3.5 | "   | 10  | 180 |
| 32 | Y | 3.5 | "   | 9.5 | 210 |
| 34 | Y | 3.5 | "   | 9.7 | 220 |

What is claimed is:

1. A method of producing a useful high-molecular-weight substance by culturing animal cells capable of proliferation in a culture tank, which comprises
   (A) a culturing step of culturing said animal cells in a culture medium in suspension to form a suspension culture mixture containing the animal cells and a useful high-molecular-weight substance produced by the animal cells;
   (B) a separating step of separating the animal cells from the suspension culture mixture and withdrawing the culture medium not containing the animal cells from the culture tank, said separation step being carried out either in the culture tank to retain said animal cells in the culture tank or outside the culture tank to recycle said animal cells into the culture tank;

(C) a removing step of removing low-molecular-weight substances inhibiting the growth of the animal cells from the culture medium by ultrafiltration, said inhibitor substances being metabolites of the animal cells and being different from the useful high-molecular-weight substance;

(D) a recycling step of recycling part or the whole of the culture medium left after removal of the growth-inhibiting low-molecular-weight substances to the culturing step (A), said recycled culture medium containing the useful high-molecular-weight substance and a growth-promoting substance;

(E) a repeating step of repeating the steps (B), (C) and (D) until the suspension culture mixture of step (A) contains an increased concentration of the useful high-molecular-weight substance; and (F) a recovering step of recovering the useful high-molecular-weight substance produced by the animal cells and accumulated in the suspension culture mixture.

2. The method of claim 1 wherein said animal cells are hybridoma cells.

3. The method of claim 1 wherein the separating step (B) is carried out by gravity sedimentation, centrifugal sedimentation or filtration.

4. The method of claim 1 wherein the low-molecular-weight substances inhibiting the growth of said animal cells have a molecular weight of 10,000 at the highest.

5. The method of claim 1 wherein said animal cells produce a useful high-molecular-weight substance having a molecular weight of more than 10,000 in the suspension culture mixture, and the culture fluid obtained in the removing step (C) contains said useful high-molecular-weight substance.

6. The method of claim 5 wherein the high-molecular-weight substance is a protein.

7. The method of claim 5 wherein the high-molecular-weight substance is an immunoglobulin.

8. The method of claim 5 wherein the high-molecular-weight substance is immunoglobulin G (IgG).

9. The method of claim 5 wherein the high-molecular-weight substance is a human immunoglobulin.

10. The method of claim 1 wherein the suspension culture mixture containing said animal cells is substantially serum-free.

11. The method of claim 1 wherein the suspension culture mixture containing said animal cells contains a substance capable of promoting the growth of the animal cells.

12. The method of claim 1 wherein the suspension culture mixture containing said animal cells contains a substance capable of promoting the growth of the animal cells, and the culture fluid obtained in the removing step (C) contains the growth-promoting substance.

13. The method of claim 1 wherein the suspension culture mixture containing the proliferating animal cells contains a substance capable of promoting the growth of the animal cells, the animal cells produce a useful high-molecular-weight substance having a molecular weight of more than 10,000, and the culture fluid obtained in the removing step (C) contains said useful high-molecular-weight substance.

14. The method of claim 11 wherein the growth promoting substance is transferin, insulin, albumin, ethanolamine or a selenium compound.

15. The method of claim 12 wherein the growth promoting substance is transferin, albumin or insulin.

* * * * *